(12) United States Patent
Hofer

(10) Patent No.: US 7,241,720 B2
(45) Date of Patent: Jul. 10, 2007

(54) HERBICIDAL COMPOSITION

(75) Inventor: Urs Hofer, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 315 days.

(21) Appl. No.: 10/490,970

(22) PCT Filed: Sep. 26, 2002

(86) PCT No.: PCT/EP02/10829

§ 371 (c)(1),
(2), (4) Date: Mar. 25, 2004

(87) PCT Pub. No.: WO03/028466

PCT Pub. Date: Apr. 10, 2003

(65) Prior Publication Data

US 2004/0266624 A1    Dec. 30, 2004

(30) Foreign Application Priority Data

Sep. 27, 2001  (CH) ..................... 1781/01

(51) Int. Cl.
*A01N 43/60* (2006.01)
*A01N 43/00* (2006.01)
(52) U.S. Cl. ..................... 504/136; 504/139
(58) Field of Classification Search ............. 504/105, 504/106, 136, 139
See application file for complete search history.

(56) References Cited

U.S. PATENT DOCUMENTS

| 6,001,774 | A | 12/1999 | Mito ..................... 504/130 |
| 6,555,499 | B1 | 4/2003 | Glock et al. |
| 6,894,005 | B1 | 5/2005 | Maetzke et al. |
| 6,962,894 | B1 | 11/2005 | Glock |
| 2005/0164883 | A1 | 7/2005 | Maetzke et al. |
| 2005/0164886 | A1 | 7/2005 | Glock |
| 2005/0187110 | A1 | 8/2005 | Maetzke et al. |

FOREIGN PATENT DOCUMENTS

| FR | 2781983 | 2/2000 |
| WO | 9824320 | 6/1998 |
| WO | 0003597 | 1/2000 |
| WO | 0117351 | 3/2001 |
| WO | 0117352 | 3/2001 |
| WO | 2003067984 | 8/2003 |

OTHER PUBLICATIONS

U.S. Appl. No. 10/070,936; Inventor: Jutta Glock; Filing or 371 Date: Aug. 9, 2002; Confirmation No. 4690.

*Primary Examiner*—Alton Pryor
(74) *Attorney, Agent, or Firm*—Jacqueline Haley

(57) ABSTRACT

Herbicidal composition comprising: a) a herbicidally effective amount of a compound of formula (I), wherein the substituents are as defined in claim 1; and b) an amount, effective for herbicide synergy, of mesosulfuron, mesotrione or flufenacet.

5 Claims, No Drawings

HERBICIDAL COMPOSITION

This application claims foreign priority to Switzerland application 1781/01 filed Sep. 27, 2001.

The present invention relates to new herbicidal compositions for controlling grasses and weeds in crops of useful plants, especially in crops of maize and cereals, which compositions comprise a tetrahydropyrazolodione herbicide known from, for example, WO 99/47525, and a co-herbicide.

The present invention relates to a herbicidal composition that, in addition to comprising customary inert formulation adjuvants, such as carriers, solvents and wetting agents, comprises as active ingredient a mixture of a) a herbicidally effective amount of a compound of formula I

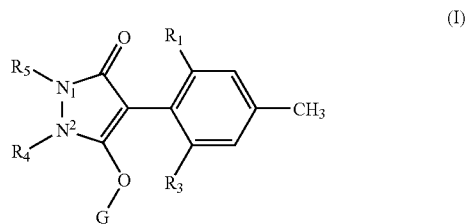

(I)

wherein $R_1$ and $R_3$ are, each independently of the other, halogen, nitro, cyano, $C_1$-$C_4$alkyl, $C_2$-$C_4$-alkenyl, $C_2$-$C_4$alkynyl, $C_1$-$C_4$haloalkyl, $C_2$-$C_6$haloalkenyl, $C_3$-$C_6$cycloalkyl, halo-substituted $C_3$-$C_6$cycloalkyl, $C_2$-$C_6$alkoxyalkyl, $C_2$-$C_6$alkylthioalkyl, hydroxy, mercapto, $C_1$-$C_6$alkoxy, $C_3$-$C_6$alkenyloxy, $C_3$-$C_6$alkynyloxy, carbonyl, carboxyl, $C_1$-$C_4$alkylcarbonyl, $C_1$-$C_4$hydroxyalkyl, $C_1$-$C_4$alkoxycarbonyl, $C_1$-$C_4$alkylthio, $C_1$-$C_4$alkylsulfinyl, $C_1$-$C_4$alkylsulfonyl, amino, $C_1$-$C_4$alkylamino or di($C_1$-$C_4$alkyl)amino;

$R_4$ and $R_5$ together are a group
—C—$R_6(R_7)$—O—C—$R_8(R_9)$—C—$R_{10}(R_{11})$—C—$R_{12}(R_{13})$— ($Z_1$),
—C—$R_{14}(R_{15})$—C—$R_{16}(R_{17})$—O—C—$R_{18}(R_{19})$—C—$R_{20}(R_{21})$— ($Z_2$), or
—C—$R_{22}(R_{23})$—C—$R_{24}(R_{25})$—C—$R_{26}(R_{27})$—O—C—$R_{28}(R_{29})$— ($Z_3$), wherein $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$ and $R_{29}$ are, each independently of the others, hydrogen, halogen, $C_1$-$C_4$alkyl or $C_1$-$C_4$haloalkyl, it being possible for an alkylene ring, which together with the carbon atoms of the groups $Z_1$, $Z_2$ or $Z_3$ contains from 2 to 6 carbon atoms and which may be interrupted by oxygen, to be either fused or spiro-bound to the carbon atoms of the groups $Z_1$, $Z_2$ or $Z_3$, or that alkylene ring bridges at least one ring atom of the groups $Z_1$, $Z_2$ or $Z_3$;

G is hydrogen, —C($X_1$)—$R_{30}$, —C($X_2$)—$X_3$—$R_{31}$, —C($X_4$)—N($R_{32}$)—$R_{33}$, —SO$_2$—$R_{34}$, an alkali metal, alkaline earth metal, sulfonium or ammonium cation, or —P($X_5$)($R_{35}$)—$R_{36}$ or —CH$_2$—X—$R_{37}$;

$X_1$, $X_2$, $X_3$, $X_4$, $X_5$ and $X_6$ are, each independently of the others, oxygen or sulfur;

$R_{30}$, $R_{31}$, $R_{32}$ and $R_{33}$ are, each independently of the others, hydrogen, $C_1$-$C_{10}$alkyl, $C_1$-$C_{10}$-haloalkyl, $C_1$-$C_{10}$cyanoalkyl, $C_1$-$C_{10}$nitroalkyl, $C_1$-$C_{10}$aminoalkyl, $C_1$-$C_5$alkylamino-$C_1$-$C_5$alkyl, $C_2$-$C_8$dialkylamino-$C_1$-$C_5$alkyl, $C_3$-$C_7$cycloalkyl-$C_1$-$C_5$alkyl, $C_2$-$C_{10}$alkoxy-alkyl, $C_4$-$C_{10}$-alkenyloxy-alkyl, $C_4$-$C_{10}$alkynyloxy-alkyl, $C_2$-$C_{10}$alkylthio-alkyl, $C_1$-$C_5$alkysulfoxyl-$C_1$-$C_5$alkyl, $C_1$-$C_5$alkylsulfonyl-$C_1$-$C_5$alkyl, $C_2$-$C_8$alkylideneamino-oxy-$C_1$-$C_5$alkyl, $C_1$-$C_5$alkylcarbonyl-$C_1$-$C_5$alkyl, $C_1$-$C_5$alkoxycarbonyl-$C_1$-$C_5$alkyl, $C_1$-$C_5$amino-carbonyl-$C_1$-$C_5$alkyl, $C_2$-$C_8$dialkyl-amino-carbonyl-$C_1$-$C_5$alkyl, $C_1$-$C_5$alkylcarbonylamino-$C_1$-$C_5$alkyl, $C_2$-$C_5$alkylcarbonyl-($C_1$-$C_5$-alkyl)-aminoalkyl, $C_3$-$C_6$trialkylsilyl-$C_1$-$C_5$alkyl, phenyl-$C_1$-$C_5$alkyl, heteroaryl-$C_1$-$C_5$alkyl, phenoxy-$C_1$-$C_5$alkyl, heteroaryloxy-$C_1$-$C_5$alkyl, $C_2$-$C_5$alkenyl, $C_2$-$C_5$haloalkenyl, $C_3$-$C_8$cyclo-alkyl, phenyl, or $C_1$-$C_3$alkyl-, $C_1$-$C_3$haloalkyl-, $C_1$-$C_3$alkoxy-, $C_1$-$C_3$haloalkoxy-, halo-, cyano- or nitro-substituted phenyl or heteroaryl or heteroarylamino, $C_1$-$C_3$alkyl-, $C_1$-$C_3$haloalkyl-, $C_1$-$C_3$-alkoxy-, $C_1$-$C_3$haloalkoxy-, halo-, cyano- or nitro-substituted heteroarylamino, diheteroaryl-amino, $C_1$-$C_3$alkyl-, $C_1$-$C_3$haloalkyl-, $C_1$-$C_3$alkoxy-, $C_1$-$C_3$haloalkoxy-, halo-, cyano- or nitro-substituted diheteroarylamino, phenylamino, $C_1$-$C_3$alkyl-, $C_1$-$C_3$haloalkyl-, $C_1$-$C_3$alkoxy-, $C_1$-$C_3$haloalkoxy-, halo-, cyano- or nitro-substituted phenylamino, diphenylamino, $C_1$-$C_3$alkyl-, $C_1$-$C_3$haloalkyl-, $C_1$-$C_3$alkoxy-, $C_1$-$C_3$haloalkoxy-, halo-, cyano- or nitro-substituted diphenyl-amino, amino, $C_3$-$C_7$cycloalkylamino, $C_1$-$C_3$alkyl-, $C_1$-$C_3$haloalkyl-, $C_1$-$C_3$alkoxy-, $C_1$-$C_3$haloalkoxy-, halo-, cyano- or nitro-substituted $C_3$-$C_7$cycloalkylamino, di-$C_3$-$C_7$cycloalkylamino, $C_1$-$C_3$alkyl-, $C_1$-$C_3$haloalkyl-, $C_1$-$C_3$alkoxy-, $C_1$-$C_3$haloalkoxy-, halo-, cyano- or nitro-substituted di-$C_3$-$C_7$-cycloalkylamino, $C_3$-$C_7$cycloalkoxy or $C_1$-$C_3$alkyl-, $C_1$-$C_3$haloalkyl-, $C_1$-$C_3$alkoxy-, $C_1$-$C_3$halo-alkoxy-, halo-, cyano- or nitro-substituted $C_3$-$C_7$cycloalkoxy;

$R_{34}$, $R_{35}$ and $R_{36}$ are, each independently of the others, hydrogen, $C_1$-$C_{10}$alkyl, $C_1$-$C_{10}$halo-alkyl, $C_1$-$C_{10}$cyanoalkyl, $C_1$-$C_{10}$nitroalkyl, $C_1$-$C_{10}$aminoalkyl, $C_1$-$C_5$alkylamino-$C_1$-$C_5$alkyl, $C_2$-$C_8$dialkylamino-$C_1$-$C_5$alkyl, $C_3$-$C_7$cycloalkyl-$C_1$-$C_5$alkyl, $C_2$-$C_{10}$alkoxy-alkyl, $C_4$-$C_{10}$-alkenyloxy-alkyl, $C_4$-$C_{10}$alkynyloxy-alkyl, $C_2$-$C_{10}$alkylthio-alkyl, $C_1$-$C_5$alkysulfoxyl-$C_1$-$C_5$alkyl, $C_1$-$C_5$alkylsulfonyl-$C_1$-$C_5$alkyl, $C_2$-$C_8$alkylideneamino-oxy-$C_1$-$C_5$alkyl, $C_1$-$C_5$alkylcarbonyl-$C_1$-$C_5$alkyl, $C_1$-$C_5$alkoxycarbonyl-$C_1$-$C_5$alkyl, $C_1$-$C_5$amino-carbonyl-$C_1$-$C_5$alkyl, $C_2$-$C_8$dialkyl-amino-carbonyl-$C_1$-$C_5$alkyl, $C_1$-$C_5$alkylcarbonylamino-$C_1$-$C_5$alkyl, $C_2$-$C_5$alkylcarbonyl-($C_1$-$C_5$-alkyl)-aminoalkyl, $C_3$-$C_6$trialkylsilyl-$C_1$-$C_5$alkyl, phenyl-$C_1$-$C_5$alkyl, heteroaryl-$C_1$-$C_5$alkyl, phenoxy-$C_1$-$C_5$alkyl, heteroaryloxy-$C_1$-$C_5$alkyl, $C_2$-$C_5$alkenyl, $C_2$-$C_5$haloalkenyl, $C_3$-$C_8$cyclo-alkyl, phenyl, or $C_1$-$C_3$alkyl-, $C_1$-$C_3$haloalkyl-, $C_1$-$C_3$alkoxy-, $C_1$-$C_3$haloalkoxy-, halo-, cyano- or nitro-substituted phenyl or heteroaryl or heteroarylamino, $C_1$-$C_3$alkyl-, $C_1$-$C_3$haloalkyl-, $C_1$-$C_3$-alkoxy-, $C_1$-$C_3$haloalkoxy-, halo-, cyano- or nitro-substituted heteroarylamino, diheteroaryl-amino, $C_1$-$C_3$alkyl-, $C_1$-$C_3$haloalkyl-, $C_1$-$C_3$alkoxy-, $C_1$-$C_3$haloalkoxy-, halo-, cyano- or nitro-substituted diheteroarylamino, phenylamino, $C_1$-$C_3$alkyl-, $C_1$-$C_3$haloalkyl-, $C_1$-$C_3$alkoxy-, $C_1$-$C_3$haloalkoxy-, halo-, cyano- or nitro-substituted phenylamino, diphenylamino, $C_1$-$C_3$alkyl-, $C_1$-$C_3$haloalkyl-, $C_1$-$C_3$alkoxy-, $C_1$-$C_3$haloalkoxy-, halo-, cyano- or nitro-substituted diphenyl-amino, $C_3$-$C_7$cycloalkylamino, $C_1$-$C_3$alkyl-, $C_1$-$C_3$haloalkyl-, $C_1$-$C_3$alkoxy-, $C_1$-$C_3$haloalkoxy-, halo-, cyano- or nitro-substituted $C_3$-$C_7$cycloalkylamino, di-$C_3$-$C_7$cycloalkylamino, $C_1$-$C_3$alkyl-, $C_1$-$C_3$haloalkyl-, $C_1$-$C_3$alkoxy-, $C_1$-$C_3$haloalkoxy-, halo-, cyano- or nitro-substituted di-$C_3$-$C_7$-cycloalkylamino, $C_3$-$C_7$cycloalkoxy, $C_1$-$C_3$alkyl-, $C_1$-$C_3$haloalkyl-, $C_1$-$C_3$alkoxy-, $C_1$-$C_3$haloalkoxy-, halo-, cyano- or nitro-substituted $C_3$-$C_7$cycloalkoxy, $C_1$-$C_{10}$alkoxy, $C_1$-$C_{10}$haloalkoxy, $C_1$-$C_5$alkylamino, $C_2$-$C_8$dialkylamino and benzyloxy or phenoxy, it being possible for the benzyl and phenyl groups themselves to be substituted by $C_1$-$C_3$alkyl, $C_1$-$C_3$haloalkyl, $C_1$-$C_3$-alkoxy, $C_1$-$C_3$haloalkoxy, halogen, cyano, formyl, acetyl, propionyl, carboxyl, $C_1$-$C_5$alkoxy-carbonyl, methylthio, ethylthio or by nitro; and $R_{37}$ is $C_1$-$C_{10}$alkyl, $C_1$-$C_{10}$haloalkyl, $C_1$-$C_{10}$cyanoalkyl, $C_1$-$C_{10}$nitroalkyl, $C_1$-$C_{10}$aminoalkyl, $C_1$-$C_5$alkylamino-$C_1$-$C_5$alkyl, $C_2$-$C_8$dialkylamino-$C_1$-$C_5$alkyl, $C_3$-$C_7$cycloalkyl-$C$-$_1$-$C_5$alkyl, $C_2$-$C_{10}$alkoxy-alkyl, $C_4$-$C_{10}$alkenyloxy-alkyl, $C_4$-$C_{10}$alkynyloxy-alkyl, $C_2$-$C_{10}$alkylthio-alkyl, $C_1$-$C_5$alkysulfoxyl-$C_1$-$C_5$alkyl, $C_1$-$C_5$alkylsulfonyl-$C_1$-$C_5$alkyl, $C_2$-$C_8$alkylideneamino-oxy-$C_1$-$C_5$alkyl, $C_1$-$C_5$alkylcarbonyl-$C_1$-$C_5$alkyl, $C_1$-$C_5$alkoxycarbonyl-$C_1$-$C_5$alkyl, $C_1$-$C_5$amino-carbonyl-$C_1$-$C_5$alkyl, $C_2$-$C_8$dialkylamino-carbonyl-$C_1$-$C_5$alkyl, $C_1$-$C_5$alkylcarbonylamino-$C_1$-$C_5$-alkyl, $C_2$-$C_5$alkylcarbonyl-($C_1$-$C_5$alkyl)-aminoalkyl, $C_3$-$C_6$trialkylsilyl-$C_1$-$C_5$-alkyl, phenyl-$C_1$-$C_5$-alkyl, heteroaryl-$C_1$-$C_5$alkyl, phenoxy-$C_1$-$C_5$alkyl, heteroaryloxy-$C_1$-$C_5$alkyl, $C_2$-$C_5$alkenyl, $C_2$-$C_5$haloalkenyl, $C_3$-$C_8$cycloalkyl, phenyl, or $C_1$-$C_3$alkyl-, $C_1$-$C_3$haloalkyl-, $C_1$-$C_3$alkoxy-, $C_1$-$C_3$haloalkoxy-, halo-, cyano- or nitro-substituted phenyl or heteroaryl, or heteroarylamino, $C_1$-$C_3$alkyl-, $C_1$-$C_3$haloalkyl-, $C_1$-$C_3$alkoxy-, $C_1$-$C_3$haloalkoxy-, halo-, cyano- or nitro-substituted heteroarylamino, diheteroarylamino, $C_1$-$C_3$alkyl-, $C_1$-$C_3$haloalkyl-, $C_1$-$C_3$alkoxy-, $C_1$-$C_3$haloalkoxy-, halo-, cyano- or nitro-substituted diheteroarylamino, phenylamino, $C_1$-$C_3$alkyl-, $C_1$-$C_3$haloalkyl-, $C_1$-$C_3$alkoxy, $C_1$-$C_3$haloalkoxy-, halo-, cyano- or nitro-substituted phenyl-amino, diphenylamino, $C_1$-$C_3$alkyl-, $C_1$-$C_3$haloalkyl-, $C_1$-$C_3$alkoxy-, $C_1$-$C_3$haloalkoxy-, halo-, cyano- or nitro-substituted diphenylamino, $C_3$-$C_7$cycloalkylamino, $C_1$-$C_3$alkyl-, $C_1$-$C_3$haloalkyl-, $C_1$-$C_3$alkoxy-, $C_1$-$C_3$haloalkoxy-, halo-, cyano- or nitro-substituted $C_3$-$C_7$cycloalkylamino, di-$C_3$-$C_7$cycloalkylamino, $C_1$-$C_3$alkyl-, $C_1$-$C_3$haloalkyl-, $C_1$-$C_3$alkoxy-, $C_1$-$C_3$haloalkoxy-, halo-, cyano- or nitro-substituted di-$C_3$-$C_7$cycloalkylamino, $C_3$-$C_7$cycloalkoxy, $C_1$-$C_3$alkyl-, $C_1$-$C_3$-haloalkyl-, $C_1$-$C_3$alkoxy-, $C_1$-$C_3$haloalkoxy-, halo-, cyano- or nitro-substituted $C_3$-$C_7$cyclo-alkoxy or $C_1$-$C_{10}$alkylcarbonyl; and salts and diastereoisomers of the compounds of formula I, with the proviso that $R_1$ and $R_3$ are not simultaneously methyl; and b) an amount, effective for herbicide synergy, of at least one herbicide selected from mesosulfuron, mesotrione and flufenacet.

In the above definitions, halogen is to be understood as fluorine, chlorine, bromine or iodine, preferably fluorine, chlorine or bromine. The alkyl groups occurring in the substituent definitions are, for example, methyl, ethyl, n-propyl, isopropyl, n-butyl, sec-butyl, isobutyl or tert-butyl, and the pentyl and hexyl isomers. Suitable cycloalkyl substituents contain from 3 to 6 carbon atoms and are, for example, cyclopropyl, cyclobutyl, cyclopentyl or cyclohexyl. They may be substituted one or more times by halogen, preferably fluorine, chlorine or bromine. Alkenyl is to be understood as, for example, vinyl, allyl, methallyl, 1-methylvinyl or but-2-en-1-yl. Alkynyl is, for example, ethynyl, propargyl, but-2-yn-1-yl, 2-methylbutyn-2-yl or but-3-yn-2-yl. Haloalkyl groups preferably have a chain length of from I to 4 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, penta-fluoroethyl, 1,1-difluoro-2,2,2-trichloroethyl, 2,2,3,3-tetrafluoroethyl or 2,2,2-trichloroethyl, preferably trichloromethyl, difluorochloromethyl, difluoromethyl, trifluoromethyl or dichloro-fluoromethyl. Suitable haloalkenyl radicals include alkenyl groups substituted one or more times by halogen, halogen being fluorine, chlorine, bromine or iodine and especially fluorine or chlorine, for example 2,2-difluoro-1-methylvinyl, 3-fluoropropenyl, 3-chloropropenyl, 3-bromopropenyl, 2,3,3-trifluoropropenyl, 2,3,3-trichloropropenyl and 4,4,4-trifluorobut-2-en-1-yl. Among the $C_2$-$C_6$alkenyl groups substituted once, twice or three times by halogen preference is given to those having a chain length of from 3 to 5 carbon atoms. Alkoxy groups preferably have a chain length of from 1 to 6 carbon atoms. Alkoxy is, for example, methoxy, ethoxy, propoxy, isopropoxy, n-butoxy, isobutoxy, sec-butoxy or tert-butoxy, or a pentyloxy or hexyloxy isomer, preferably methoxy or ethoxy. Alkylcarbonyl is preferably acetyl or propionyl. Alkoxycarbonyl is, for example, methoxycarbonyl, ethoxycarbonyl, propoxycarbonyl, isopropoxycarbonyl, n-butoxycarbonyl, isobutoxycarbonyl, sec-butoxy-carbonyl or tert-butoxycarbonyl, preferably methoxycarbonyl or ethoxycarbonyl. Alkylthio groups preferably have a chain length of from 1 to 4 carbon atoms. Alkylthio is, for example, methylthio, ethylthio, propylthio, isopropylthio, n-butylthio, isobutylthio, sec-butylthio or tert-butylthio, preferably methylthio or ethylthio. Alkylsulfinyl is, for example, methylsulfinyl, ethyl-sulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl. Alkylsulfonyl is, for example, methylsulfonyl, ethylsulfonyl, propylsulfonyl, isopropylsulfonyl, n-butylsulfonyl, isobutyl-sulfonyl, sec-butylsulfonyl or tert-butylsulfonyl, preferably methylsulfonyl or ethylsulfonyl. Alkylamino is, for example, methylamino, ethylamino, n-propylamino, isopropylamino or a butylamine isomer. Dialkylamino is, for example, dimethylamino, methylethylamino, diethyl-amino, n-propylmethylamino, dibutylamino or diisopropylamino. Alkoxyalkyl groups preferably have from 2 to 6 carbon atoms. Alkoxyalkyl is, for example, methoxymethyl, methoxyethyl, ethoxymethyl, ethoxyethyl, n-propoxymethyl, n-propoxyethyl, isopropoxy-methyl or isopropoxyethyl. Alkylthioalkyl is, for example, methylthiomethyl, methylthioethyl, ethylthiomethyl, ethylthioethyl, n-propylthiomethyl, n-propylthioethyl, isopropylthiomethyl, isopropylthioethyl, butylthiomethyl, butylthioethyl or butylthiobutyl. Phenyl may be in substituted form, in which case the substituents may be in the ortho-, meta- and/or para-position. Preferred positions for the substituents are the ortho- and para-positions to the ring attachment point. Heteroaryl groups are usually aromatic heterocycles that contain preferably from 1 to 3 hetero atoms selected from nitrogen, oxygen and sulfur. Examples of suitable heterocycles and heteroaromatic compounds are: pyrrolidine, piperidine, pyran, dioxane, azetidine, oxetane, pyridine, pyrimidine, triazine, thiazole, thiadiazole, imidazole, oxazole, isoxazole and pyrazine, furan, morpholine, piperazine, pyrazole, benzoxazole, benzothiazole, quinoxaline and quinoline. Those heterocycles and heteroaromatic compounds may be further substituted, for example by halogen, alkyl, alkoxy, haloalkyl, haloalkoxy, nitro, cyano, thioalkyl, alkylamino or by phenyl. The $C_2$-$C_{10}$-alkenyl and -alkynyl groups $R_{34}$ may be mono- or poly-unsaturated. They contain preferably from 2 to 12 carbon atoms, especially from 2 to 6 carbon atoms.

Alkali metal, alkaline earth metal or ammonium cations for the substituent G are, for example, the cations of sodium, potassium, magnesium, calcium and ammonium: Preferred sulfonium cations are especially trialkylsulfonium cations wherein the alkyl radicals each contain preferably from 1 to 4 carbon atoms.

The left-hand free valence of the groups $Z_1$, $Z_2$ and $Z_3$ is bound to the 1-position and the right-hand free valence to the 2-position of the pyrazoline ring.

Compounds of formula I wherein it is possible for an alkylene ring, which together with the carbon atoms of the groups $Z_1$, $Z_2$ and $Z_3$ contains from 2 to 6 carbon atoms, to be fused or spiro-bound to the groups $Z_1$, $Z_2$ and $Z_3$ have, for example, the following structure:

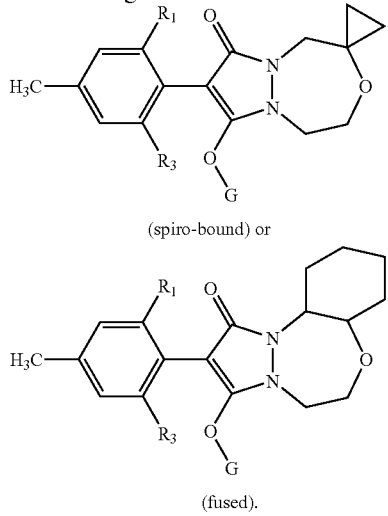

(spiro-bound) or (fused).

Compounds of formula I wherein in the groups $Z_1$, $Z_2$ or $Z_3$ an alkylene ring bridges at least one ring atom of the groups $Z_1$, $Z_2$ or $Z_3$, have, for example, the following structure:

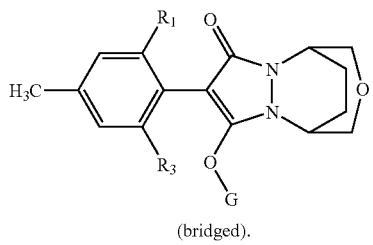

(bridged).

Flufenacet is known from The Pesticide Manual, 12th Edition (BCPC) 2000, Entry No. 362; mesotrione is known from The Pesticide Manual, 12th Edition (BCPC) 2000, Entry No. 500; mesosulfuron is described, for example, in WO 00/3591 and WO 01/24633.

In herbicides of formula I that are preferred for the compositions in accordance with the invention, $R_1$ and $R_3$ are, each independently of the other, ethyl, haloethyl, ethynyl, $C_1$-$C_2$-alkoxy or $C_1$-$C_2$haloalkoxy.

Preference is given also to those compositions in accordance with the invention wherein, in the herbicides of formula I, $R_4$ and $R_5$ together are a $Z_2$ group —C—$R_{14}(R_{15})$—C—$R_{16}(R_{17})$—O—C—$R_{18}(R_{19})$—C—$R_{20}(R_{21})$—($Z_2$) wherein $R_{14}$, $R_{15}$, $R_{16}$, $R_{17}$, $R_{18}$, $R_{19}$, $R_{20}$ and $R_{21}$ are especially preferably hydrogen.

In a further preferred group of compositions according to the invention, in the herbicides of formula I $R_{30}$, $R_{31}$, $R_{32}$ and $R_{33}$ are, each independently of the others, hydrogen, $C_1$-$C_8$alkyl, $C_1$-$C_8$haloalkyl, $C_1$-$C_8$cyanoalkyl, $C_1$-$C_8$nitroalkyl, $C_1$-$C_8$aminoalkyl, $C_2$-$C_5$alkenyl, $C_2$-$C_5$halo-alkenyl, $C_3$-$C_8$cycloalkyl, $C_1$-$C_5$alkylamino-$C_1$-$C_5$alkyl, $C_2$-$C_8$dialkylamino-$C_1$-$C_5$alkyl, $C_3$-$C_7$-cycloalkyl-$C_1$-$C_5$alkyl, $C_2$-$C_4$alkoxy-alkyl, $C_4$-$C_6$alkenyloxy-alkyl, $C_4$-$C_6$alkynyloxy-alkyl, $C_2$-$C_4$alkylthio-alkyl, $C_1$-$C_4$alkysulfinyl-$C_1$-$C_2$alkyl, $C_1$-$C_2$alkylsulfonyl-$C_1$-$C_2$alkyl, $C_2$-$C_4$alkyl-ideneamino-oxy-$C_1$-$C_2$alkyl, $C_1$-$C_5$alkylcarbonyl-$C_1$-$C_2$alkyl, $C_1$-$C_5$alkoxycarbonyl-$C_1$-$C_2$alkyl, $C_1$-$C_5$amino-carbonyl-$C_1$-$C_2$alkyl, $C_2$-$C_8$dialkylamino-carbonyl-$C_1$-$C_2$alkyl, $C_1$-$C_5$alkylcarbonyl-amino-$C_1$-$C_2$alkyl, $C_2$-$C_5$alkylcarbonyl-($C_1$-$C_2$alkyl)-aminoalkyl, $C_3$-$C_6$trialkylsilyl-$C_1$-$C_5$alkyl, phenyl-$C_1$-$C_2$alkyl, heteroaryl-$C_1$-$C_2$alkyl, phenoxy-$C_1$-$C_2$alkyl, heteroaryloxy-$C_1$-$C_2$alkyl, phenyl or heteroaryl;

$R_{34}$, $R_{35}$ and $R_{36}$, are each independently of the others, hydrogen, $C_1$-$C_8$alkyl, $C_1$-$C_8$haloalkyl, $C_1$-$C_8$cyanoalkyl, $C_1$-$C_8$nitroalkyl, $C_1$-$C_8$aminoalkyl, $C_2$-$C_5$alkenyl, $C_2$-$C_5$haloalkenyl, $C_3$-$C_8$-cycloalkyl, $C_1$-$C_5$alkylamino-$C_1$-$C_5$alkyl, $C_2$-$C_8$dialkylamino-$C_1$-$C_5$alkyl, $C_3$-$C_7$cycloalkyl-$C_1$-$C_5$-alkyl, $C_2$-$C_4$alkoxy-alkyl, $C_4$-$C_6$alkenyloxy-alkyl, $C_4$-$C_6$alkynyloxy-alkyl, $C_2$-$C_4$alkylthio-alkyl, $C_1$-$C_4$alkysulfinyl-$C_1$-$C_2$alkyl, $C_1$-$C_2$alkylsulfonyl-$C_1$-$C_2$alkyl, $C_2$-$C_4$alkylideneamino-oxy-$C_1$-$C_2$alkyl, $C_1$-$C_5$alkylcarbonyl-$C_1$-$C_2$alkyl, $C_1$-$C_5$alkoxycarbonyl-$C_1$-$C_2$alkyl, $C_1$-$C_5$amino-carbonyl-$C_1$-$C_2$alkyl, $C_2$-$C_8$dialkylamino-carbonyl-$C_1$-$C_2$alkyl, $C_1$-$C_5$alkylcarbonylamino-$C_1$-$C_2$-alkyl, $C_2$-$C_5$alkylcarbonyl-($C_1$-$C_2$alkyl)-aminoalkyl, $C_3$-$C_6$trialkylsilyl-$C_1$-$C_5$alkyl, phenyl-$C_1$-$C_2$-alkyl, heteroaryl-$C_1$-$C_2$alkyl, phenoxy-$C_1$-$C_2$alkyl, heteroaryloxy-$C_1$-$C_2$alkyl, phenyl or heteroaryl, benzyloxy or phenoxy, it being possible for the benzyl and phenyl groups themselves to be substituted by halogen, nitro, cyano, amino, dimethylamino, hydroxy, methoxy, ethoxy, methylthio, ethylthio, formyl, acetyl, propionyl, carboxyl, $C_1$-$C_5$alkoxy-carbonyl or by $C_1$— or $C_2$-haloalkyl; and $R_{37}$ is $C_1$-$C_8$alkyl, $C_1$-$C_8$haloalkyl, $C_1$-$C_8$cyanoalkyl, $C_1$-$C_8$nitroalkyl, $C_1$-$C_8$aminoalkyl, $C_2$-$C_5$-alkenyl, $C_2$-$C_5$haloalkenyl, $C_3$-$C_8$cycloalkyl, $C_1$-$C_5$alkylamino-$C_1$-$C_5$alkyl, $C_2$-$C_8$dialkylamino-$C_1$-$C_5$alkyl, $C_3$-$C_7$cycloalkyl-$C_1$-$C_5$alkyl, $C_2$-$C_4$alkoxy-alkyl, $C_4$-$C_6$alkenyloxy-alkyl, $C_4$-$C_6$-alkynyloxy-alkyl, $C_2$-$C_4$alkylthio-alkyl, $C_1$-$C_4$alkylsulfinyl-$C_1$-$C_2$alkyl, $C_1$-$C_2$alkylsulfonyl-$C_1$-$C_2$-alkyl, $C_2$-$C_4$alkylideneamino-oxy-$C_1$-$C_2$alkyl, $C_1$-$C_5$alkylcarbonyl-$C_1$-$C_2$alkyl, $C_1$-$C_5$alkoxy-carbonyl-$C_1$-$C_2$alkyl, $C_1$-$C_5$amino-carbonyl-$C_1$-$C_2$alkyl, $C_2$-$C_8$dialkylamino-carbonyl-$C_1$-$C_2$alkyl, $C_1$-$C_5$alkylcarbonylamino-$C_1$-$C_2$alkyl, $C_2$-$C_5$alkylcarbonyl-($C_1$-$C_2$alkyl)-aminoalkyl, $C_3$-$C_6$trialkyl-silyl-$C_1$-$C_5$alkyl, phenyl-$C_1$-$C_2$alkyl, heteroaryl-$C_1$-$C_2$alkyl, phenoxy-$C_1$-$C_2$alkyl, heteroaryloxy-$C_1$-$C_2$alkyl, phenyl or heteroaryl, benzyloxy or phenoxy, it being possible for the benzyl and phenyl groups themselves to be substituted by halogen, nitro, cyano, amino, dimethylamino, hydroxy, methoxy, ethoxy, methylthio, ethylthio, formyl, acetyl, propionyl, carboxyl, $C_1$-$C_2$-alkoxycarbonyl or by $C_1$— or $C_2$-haloalkyl; or $R_{37}$ is $C_1$-$C_8$alkylcarbonyl.

Special preference is given to those compositions according to the invention wherein, in the herbicides of formula I, $R_{30}$, $R_{31}$, $R_{32}$ and $R_{33}$ are, each independently of the others, hydrogen, $C_1$-$C_8$alkyl, $C_1$-$C_8$haloalkyl, $C_2$-$C_5$alkenyl, $C_2$-$C_5$haloalkenyl, $C_3$-$C_8$cycloalkyl, $C_3$-$C_7$cycloalkyl-$C_1$-$C_2$alkyl, $C_2$-$C_4$alkoxy-alkyl, phenyl, heteroaryl, phenyl-$C_1$-$C_2$alkyl, heteroaryl-$C_1$-$C_2$alkyl, phenoxy-$C_1$-$C_2$alkyl, heteroaryloxy-$C_1$-$C_2$alkyl;

$R_{34}$, $R_{35}$ and $R_{36}$ are, each independently of the others, hydrogen, $C_1$-$C_8$alkyl, $C_1$-$C_8$haloalkyl, $C_2$-$C_5$alkenyl, $C_2$-$C_5$haloalkenyl, $C_3$-$C_8$cycloalkyl, $C_3$-$C_7$cycloalkyl-$C_1$-$C_2$alkyl, $C_2$-$C_4$alkoxy-alkyl, phenyl, heteroaryl, phenyl-$C_1$-$C_2$alkyl, heteroaryl-$C_1$-$C_2$alkyl, phenoxy-$C_1$-$C_2$alkyl, heteroaryloxy-$C_1$-$C_2$alkyl, $C_1$-$C_6$alkoxy, $C_1$-$C_3$alkylamino or di($C_1$-$C_3$alkyl)amino; and $R_{37}$ is $C_1$-$C_8$alkyl, $C_1$-$C_8$haloalkyl, $C_2$-$C_{-5}$alkenyl, $C_2$-$C_5$haloalkenyl, $C_3$-$C_8$cycloalkyl, $C_3$-$C_7$-cycloalkyl-$C_1$-$C_2$alkyl, $C_2$-$C_4$alkoxy-alkyl, phenyl, heteroaryl, phenyl-$C_1$-$C_2$alkyl, heteroaryl-$C_1$-$C_2$alkyl, phenoxy-$C_1$-$C_2$alkyl, heteroaryloxy-$C_1$-$C_2$alkyl, $C_1$-$C_6$alkoxy, $C_1$-$C_3$alkylamino, di-($C_1$-$C_3$alkyl)-amino or $C_1$-$C_8$alkylcarbonyl.

A further group of especially preferred compositions comprise as herbicides of formula I those wherein $R_1$ and $R_3$ are ethyl, $R_4$ and $R_5$ together are a group $Z_2$ —C—$R_{14}$($R_{15}$)—C—$R_{16}$($R_{17}$)—O—C—$R_{18}$($R_{19}$)—C—$R_{20}$($R_{21}$)—, wherein $R_{14}$, $R_{15}$, $R_{16}$, $R_{17}$, $R_{18}$, $R_{19}$, $R_{20}$ and $R_{21}$ are hydrogen, and G is hydrogen or a radical of formula —C($X_1$)—$R_{30}$ wherein $X_1$ is oxygen and $R_{30}$ is hydrogen or $C_1$-$C_8$alkyl, especially $C_4$alkyl, preferably tert-butyl.

The compositions according to the invention may also comprise salts that the compounds of formula I may form with acids. Suitable acids for the formation of acid addition salts are both organic and inorganic acids. Examples of such acids are hydrochloric acid, hydrobromic acid, nitric acid, phosphoric acids, sulfuric acid, acetic acid, propionic acid, butyric acid, valeric acid, oxalic acid, malonic acid, fumaric acid, organic sulfonic acids, lactic acid, tartaric acid, citric acid and salicylic acid. The salts of the compounds of formula I having acid hydrogen are also alkali metal salts, for example sodium and potassium salts; alkaline earth metal salts, for example calcium and magnesium salts; ammonium salts, that is to say unsubstituted ammonium salts and mono- or poly-substituted ammonium salts, or are salts with other organic nitrogen bases. Suitable salt formers are accordingly alkali metal and alkaline earth metal hydroxides, especially the hydroxides of lithium, sodium, potassium, magnesium or calcium, with those of sodium or potassium being given special importance.

Examples of suitable amines for ammonium salt formation that come into consideration are ammonia as well as primary, secondary and tertiary $C_1$-$C_{18}$alkylamines, $C_1$-$C_4$hydroxyalkyl-amines and $C_2$-$C_4$alkoxyalkylamines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methyl-ethylamine, methyl-isopropylamine, methyl-hexylamine, methyl-nonylamine, methyl-pentadecylamine, methyl-octadecylamine, ethyl-butylamine, ethyl-heptylamine, ethyl-octylamine, hexyl-heptylamine, hexyl-octylamine, dimethylamine, diethylamine, di-n-propylamine, diisopropylamine, di-n-butylamine, di-n-amylamine, diisoamylamine, dihexylamine, diheptylamine, dioctylamine, ethanolamine, n-propanolamine, isopropanolamine, N,N-diethanolamine, N-ethylpropanolamine, N-butyl-ethanolamine, allylamine, n-butenyl-2-amine, n-pentenyl-2-amine, 2,3-dimethylbutenyl-2-amine, dibutenyl-2-amine, n-hexenyl-2-amine, propylenediamine, trimethylamine, triethyl-amine, tri-n-propylamine, triisopropylamine, tri-n-butylamine, triisobutylamine, tri-sec-butylamine, tri-n-amylamine, methoxyethylamine and ethoxyethylamine; heterocyclic amines, for example pyridine, quinoline, isoquinoline, morpholine, N-methylmorpholine, thio-morpholine, piperidine, pyrrolidine, indoline, quinuclidine and azepine; primary aryl amines, for example anilines, methoxyanilines, ethoxyanilines, o-, m- and p-toluidines, phenylene-diamines, benzidines, naphthylamines and o-, m- and p-chloroanilines; but especially triethylamine, isopropylamine and diisopropylamine.

If non-chiral starting materials are employed, the asymmetrically substituted compounds of formula I obtained in the processes described in this Application are generally in the form of racemates. The stereoisomers can then be separated on the basis of their physicochemical properties according to known methods, such as, for example, fractional crystallisation following salt formation with optically pure bases, acids or metal complexes, or by chromatographic procedures, such as, for example, high-pressure liquid chromatography (HPLC) on acetyl cellulose. In the present invention, "compounds of formula I" are to be understood as including both the concentrated and optically pure forms of the stereoisomers in question and the racemates and diastereoisomers. Where no special mention is made of individual optical antipodes, the formula in question is to be understood as referring to the racemic mixtures that are obtained in the preparation process mentioned. When an aliphatic C═C double bond is present, geometric isomerism may also occur.

The compounds of formula I may, also in dependence upon the nature of the substituents, occur as geometric and/or optical isomers and isomeric mixtures and as tautomers and tautomeric mixtures. For example, the compounds of formula I wherein the group G is hydrogen can occur in the following tautomeric equilibria:

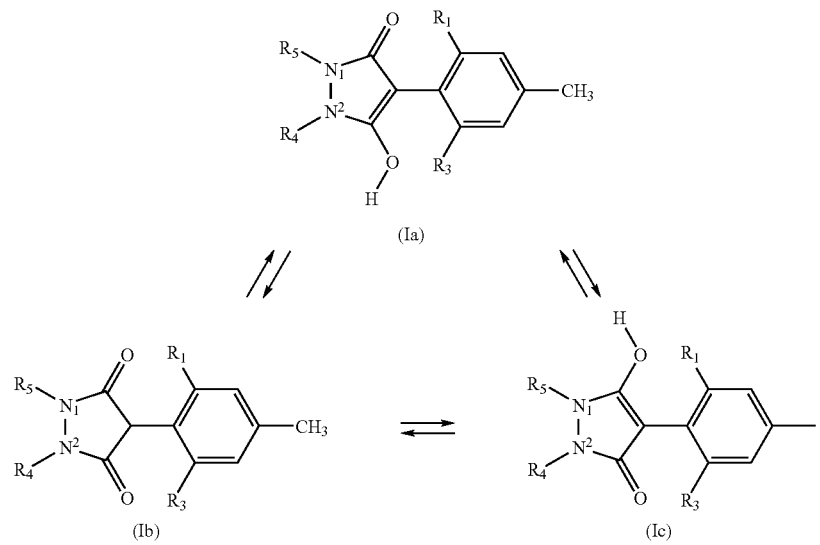

When G is other than hydrogen and Z is the group $Z_1$ or $Z_3$, or when G is other than hydrogen and $Z_2$ is asymmetrically substituted, fused or spiro-bound, the compound of formula I may occur as an isomer of formula Id

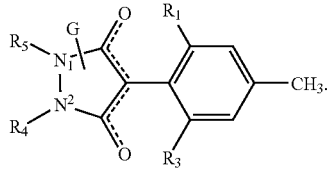
(Id)

Processes for the preparation of compounds that differ from the compounds of formula I according to the present invention in respect of the meanings of the substituents $R_4$ and $R_5$ are described, for example, in WO 96/21652. The compounds of formula I according to the present invention can be prepared analogously to the processes described in WO 99/47525 and WO 01/17351.

TABLE 1

Compounds of formula Ia
(The substituents $R_4$ and $R_5$ in the compounds of formula I
form a —$C_2H_4$—O—$C_2H_4$— radical in the compounds of formula Ia)

(Ia)

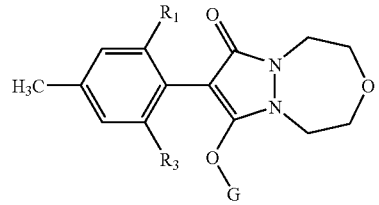

| Comp. No. | $R_1$ | $R_3$ | G | Physical data |
|---|---|---|---|---|
| 1.001 | $CH_3$ | $OCH_3$ | H | |
| 1.002 | $CH_3$ | $OCH_3$ | $C(O)C(CH_3)_3$ | |
| 1.003 | $CH_3$ | $OCH_3$ | $C(O)OCH_2CH_3$ | |
| 1.004 | $CH_2CH_3$ | $CH_3$ | H | m.p. 182–185° C. |
| 1.005 | $CH_2CH_3$ | $CH_3$ | $C(O)C(CH_3)_3$ | m.p. 110–113° C. |
| 1.006 | $CH_2CH_3$ | $CH_3$ | $C(O)OCH_2CH_3$ | |
| 1.007 | $CH_2CH_3$ | $CH_2CH_3$ | H | m.p. 189–191° C. |
| 1.008 | $CH_2CH_3$ | $CH_2CH_3$ | $C(O)C(CH_3)_3$ | m.p. 122–124° C. |
| 1.009 | $CH_2CH_3$ | $CH_2CH_3$ | $C(O)OCH_2CH_3$ | m.p. 114–116° C. |
| 1.010 | $CH=CH_2$ | $CH_3$ | H | m.p. 165–170° C. |
| 1.011 | $CH=CH_2$ | $CH_3$ | $C(O)C(CH_3)_3$ | m.p. 111–113° C. |
| 1.012 | $CH=CH_2$ | $CH_2CH_3$ | H | |
| 1.013 | $CH=CH_2$ | $CH=CH_2$ | H | |
| 1.014 | $CH=CH_2$ | $CH=CH_2$ | $C(O)C(CH_3)_3$ | |
| 1.015 | $C{\equiv}CH$ | $CH_3$ | H | m.p. 179–184° C. |
| 1.016 | $C{\equiv}CH$ | $CH_3$ | $C(O)C(CH_3)_3$ | m.p. 109–111° C. |
| 1.017 | $C{\equiv}CH$ | $CH_3$ | $C(O)OCH_2CH_3$ | |
| 1.018 | $C{\equiv}CH$ | $CH_2CH_3$ | H | m.p. 189–193° C. |
| 1.019 | $C{\equiv}CH$ | $CH_2CH_3$ | $C(O)C(CH_3)_3$ | |
| 1.020 | $C{\equiv}CH$ | $CH_2CH_3$ | $C(O)OCH_2CH_3$ | |
| 1.021 | $C{\equiv}CH$ | $C{\equiv}CH$ | H | m.p. 300° C. |
| 1.022 | $C{\equiv}CH$ | $C{\equiv}CH$ | $C(O)C(CH_3)_3$ | m.p. 183–185° C. |
| 1.023 | $C{\equiv}CH$ | $C{\equiv}CH$ | $C(O)OCH_2CH_3$ | |
| 1.024 | $C{\equiv}CH$ | $CH=CH_2$ | H | |
| 1.025 | $C{\equiv}CCH_3$ | $CH_3$ | H | m.p. 179–181° C. |
| 1.026 | $C{\equiv}CCH_3$ | $CH_3$ | $C(O)C(CH_3)_3$ | m.p. 128–129° C. |
| 1.027 | $C{\equiv}CCH_3$ | $CH_3$ | $C(O)OCH_2CH_3$ | |
| 1.028 | $C{\equiv}CCH_3$ | $CH_2CH_3$ | H | |
| 1.029 | $C{\equiv}CCH_3$ | $CH_2CH_3$ | $C(O)C(CH_3)_3$ | |
| 1.030 | $C{\equiv}CCH_3$ | $C{\equiv}CCH_3$ | H | |
| 1.031 | $C{\equiv}CCH_3$ | $C{\equiv}CCH_3$ | $C(O)C(CH_3)_3$ | |
| 1.032 | $CH_2CH_2CH_3$ | $CH_3$ | H | m.p. 136–138° C. |
| 1.033 | $CH_2CH_2CH_3$ | $CH_3$ | $C(O)C(CH_3)_3$ | m.p. 65–67° C. |
| 1.034 | $CH_2CH_2CH_3$ | $CH_3$ | $C(O)OCH_2CH_3$ | |
| 1.035 | $CH_2CH_2CH_3$ | $CH_2CH_3$ | H | |
| 1.036 | $CH_2CH_2CH_3$ | $CH_2CH_2CH_3$ | H | |
| 1.037 | $CH_2CH_2CH_3$ | $CH_2CH_2CH_3$ | $C(O)C(CH_3)_3$ | |
| 1.038 | $CH_2CH_2CH_3$ | $CH_2CH_2CH_3$ | $C(O)OCH_2CH_3$ | |
| 1.039 | $CH_2CH_2CH_3$ | $C{\equiv}CH$ | H | |
| 1.040 | $CH(CH_3)_2$ | $CH_3$ | H | m.p. 214–216° C. |
| 1.041 | $CH(CH_3)_2$ | $CH_3$ | $C(O)C(CH_3)_3$ | m.p. 148–151° C. |
| 1.042 | $CH(CH_3)_2$ | $CH_2CH_3$ | H | |

TABLE 1-continued

Compounds of formula Ia
(The substituents $R_4$ and $R_5$ in the compounds of formula I
form a —$C_2H_4$—O—$C_2H_4$— radical in the compounds of formula Ia)

(Ia)

| Comp. No. | $R_1$ | $H_3$ | G | Physical data |
|---|---|---|---|---|
| 1.043 | $CH(CH_3)_2$ | C≡CH | H | |
| 1.044 |  | $CH_3$ | H | |
| 1.045 |  | $CH_2CH_3$ | H | |
| 1.046 | 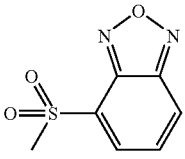 | C≡CH | H | |
| 1.047 | $CH_2CH=CH_2$ | $CH_3$ | H | |
| 1.048 | $CH_2CH=CH_2$ | $CH_2CH_3$ | H | |
| 1.049 | $CH_2CH=CH_2$ | C≡CH | H | |
| 1.050 | $CH_2CH_2CH_2CH_3$ | $CH_3$ | H | |
| 1.051 | $CH_3O$— | $CH_2CH_3$ | H | |
| 1.052 | $CH_3O$— | $CH_2CH_3$ | $C(O)C(CH_3)_3$ | |
| 1.053 | $CH_2CH_3$ | $CH_2CH_3$ | $SO_2CH(CH_3)_2$ | |
| 1.054 | $CH_2CH_3$ | $CH_2CH_3$ | $SO_2CH_3$ | crystalline |
| 1.055 | $CH_2CH_3$ | $CH_2CH_3$ | $SO_2CH(CH_3)_2$ | |
| 1.056 | $CH_2CH_3$ | $CH_2CH_3$ | $SO_2CF_3$ | |
| 1.057 | $CH_2CH_3$ | $CH_2CH_3$ | $SO_2CH_2CH_3$ | |
| 1.058 | $CH_2CH_3$ | $CH_2CH_3$ | $SO_2CH_2CH(CH_3)_2$ | wax |
| 1.059 | $CH_2CH_3$ | $CH_2CH_3$ | $SO_2CH_2CH_2Cl$ | |
| 1.060 | $CH_2CH_3$ | $CH_2CH_3$ | $SO_2CH=CH2$ | wax |
| 1.061 | $CH_2CH_3$ | $CH_2CH_3$ | $SO_2CH_2CH_2Br$ | |
| 1.062 | $CH_2CH_3$ | $CH_2CH_3$ | 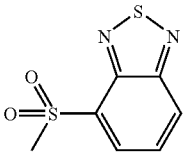 | m.p.: 204–205 |
| 1.063 | $CH_2CH_3$ | $CH_2CH_3$ | 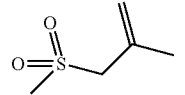 | m.p.: 203–204 |
| 1.064 | $CH_2CH_3$ | $CH_2CH_3$ | $SO_2$-benzyl | m.p.: 157–158 |
| 1.065 | $CH_2CH_3$ | $CH_2CH_3$ | | wax |
| 1.066 | $CH_2CH_3$ | $CH_2CH_3$ | $SO_2CH_2CH_2CH_2Cl$ | wax |

TABLE 1-continued

Compounds of formula Ia
(The substituents $R_4$ and $R_5$ in the compounds of formula I
form a —$C_2H_4$—O—$C_2H_4$— radical in the compounds of formula Ia)

(Ia)

| Comp. No. | $R_1$ | $H_3$ | G | Physical data |
|---|---|---|---|---|
| 1.067 | $CH_2CH_3$ | $CH_2CH_3$ | (2,4-dichloro-thiophen-3-yl sulfonyl) | m.p.: 126 |
| 1.068 | $CH_2CH_3$ | $CH_2CH_3$ | (3,5-dimethyl-isoxazol-4-yl sulfonyl) | m.p.: 146 |
| 1.069 | $CH_2CH_3$ | $CH_2CH_3$ | (5-chloro-1,3-dimethyl-pyrazol-4-yl sulfonyl) | m.p.: 82–85 |
| 1.070 | $CH_2CH_3$ | $CH_2CH_3$ | $SO_2CH_2CH{=}CH_2$ | |
| 1.071 | C≡CH | $CH_2CH_3$ | $SO_2CH_3$ | |
| 1.072 | C≡CH | $CH_2CH_3$ | $SO_2CH(CH_3)_2$ | |
| 1.073 | C≡CH | $CH_2CH_3$ | $SO_2CH_2CH_2Cl$ | |
| 1.074 | C≡CH | $CH_2CH_3$ | $SO_2CF_3$ | |
| 1.075 | C≡CH | $CH_2CH_3$ | $SO_2CH{=}CH_2$ | |
| 1.076 | C≡CH | $OCH_3$ | —H | m.p. 202–204 |
| 1.077 | C≡CH | $OCH_3$ | $C(O)C(CH_3)_3$ | m.p. 204–206 |
| 1.078 | C≡CSi$(CH_3)_3$ | $OCH_3$ | $C(O)C(CH_3)_3$ | m.p. 169–171 |
| 1.079 | C≡CSi$(CH_3)_3$ | $OCH_3$ | —H | m.p. 173–174 |
| 1.080 | Br | $OCH_3$ | —H | m.p. 217–219 |
| 1.081 | Br | $OCH_3$ | $C(O)C(CH_3)_3$ | m.p. 173–175 |
| 1.082 | $CH_2CH_3$ | $CH_2CH_3$ | $C(O)C(CH_3)_2CH_2CH_3$ | m.p. 122–124° C. |
| 1.083 | $CH_2CH_3$ | $CH_2CH_3$ | $CON(CH_2CH_3)_2$ | m.p. 82–84 |
| 1.084 | $CH_2CH_3$ | $C(O)CH_3$ | $C(O)C(CH_3)_2CH_2CH_3$ | m.p. 138–139° C. |
| 1.085 | $CH_2CH_3$ | $C(O)CH_3$ | (ethyl 2,2-dimethylpropanoate ester) | |
| 1.086 | $CH_2CH_3$ | $C(O)CH_3$ | (diethyl ether group) | |
| 1.087 | $CH_2CH_3$ | $C(O)CH_3$ | (diethyl sulfide group) | |
| 1.088 | $CH_2CH_3$ | $C(O)CH_3$ | (ethyl methyl sulfide group) | |

The rates of application of herbicide are generally from 0.001 to 2 kg/ha, but preferably from 0.005 to 1 kg/ha.

The ratio by weight of the compound of formula I to the second herbicide (mesosulfuron, mesotrione or flufenacet) in the composition according to the invention is preferably from 1:100 to 1000:1.

The compositions according to the invention preferably contain in addition a safener and, optionally, an oil additive. The present invention accordingly relates also to herbicidal compositions that, in addition to comprising customary inert formulation adjuvants, such as carriers, solvents and wetting agents, comprise as active ingredient a mixture of a) a herbicide of formula I,
b) an amount, effective for herbicide synergy, of mesosulfuron, mesotrione or flufenacet,
c) an amount, effective for herbicide antagonism, of a safener selected from cloquintocet-mexyl and mefenpyr-diethyl; and, optionally,
d) an additive comprising an oil of vegetable or animal origin, a mineral oil, alkyl esters of such oils, or mixtures of such oils and oil derivatives.

The safeners cloquintocet-mexyl and mefenpyr-diethyl can also be used in the form of their alkali metal, alkaline earth metal, sulfonium or ammonium salts. Examples thereof are described, for example, in WO 02/34048. It is also possible to use hydrates of cloquintocet-mexyl, which are mentioned in WO 02/36566.

Cultivated plants that can be protected against the harmful effect of the above-mentioned herbicide mixtures by means of such safeners are especially cereals, cotton, soybeans, sugar beet, sugar cane, plantation crops, rape, maize and rice, more especially cereals. Crops are to be understood as including those that have been made tolerant to herbicides or classes of herbicides by means of conventional breeding or genetic engineering methods.

The weeds to be controlled may be either dicotyledonous or, preferably, monocotyledonous weeds, for example the monocotyledonous weeds *Avena, Agrostis, Phalaris, Lolium, Bromus, Alopecurus, Setaria, Digitaria, Brachiaria, Echinochloa, Panicum, Sorghum* hal./bic., *Rottboellia, Cyperus, Brachiaria, Echinochloa, Scirpus, Monochoria* and *Sagittaria*, and the dicotyledonous weeds *Sinapis, Chenopodium, Stellaria, Galium, Viola, Veronica, Matricaria, Papaver, Solanum, Abutilon, Sida, Xanthium, Amaranthus, Ipomoea* and *Chrysanthemum*.

Areas of cultivation include the areas of ground on which cultivated plants are already growing or which have already been sown with the seeds of those cultivated plants, as well as ground intended for cultivation with such cultivated plants.

Depending on the intended use, a safener according to the invention can be used to pre-treat the seed material of the cultivated plant (dressing the seed or the cuttings) or can be introduced into the soil before or after sowing. It can, however, also be applied, either alone or together with the herbicide mixture and the oil additive, after the emergence of the plants. The treatment of the plants or seed with the safener can therefore, in principle, be effected independently of the time at which the herbicide mixture is applied. The treatment of the plants can, however, also be carried out by applying herbicide, oil additive and safener simultaneously (for example in the form of a tank mixture). The rate of application of safener in relation to herbicide depends largely on the method of application. In the case of field treatment, which is effected either using a tank mixture comprising a combination of safener and herbicide mixture or by separate application of safener and herbicide mixture, the ratio of herbicides to safener is generally from 100:1 to 1:10, preferably from 20:1 to 1:1. In the case of field treatment, from 0.001 to 1.0 kg of safener/ha, preferably from 0.001 to 0.25 kg of safener/ha, is generally applied.

In the composition according to the invention, the amounts of oil additive employed are generally from 0.01 to 2%, based on the spray mixture. The oil additive can, for example, be added to the spray tank in the desired concentration after the spray mixture has been prepared.

Preferred oil additives comprise mineral oils or an oil of vegetable origin such as, for example, rapeseed oil, olive oil or sunflower oil, alkyl esters of oils of vegetable origin such as, for example, the methyl derivatives, or an oil of animal origin such as fish oil or beef tallow.

Especially preferred oil additives comprise alkyl esters of higher fatty acids ($C_8$-$C_{22}$), especially the methyl derivatives of $C_{12}$-$C_{18}$ fatty acids, for example the methyl esters of lauric acid, palmitic acid and oleic acid. Those esters are known as methyl laurate (CAS-111-82-0), methyl palmitate (CAS-112-39-0) and methyl oleate (CAS-112-62-9).

The application and action of the oil additives can be improved by combining them with surface-active substances such as non-ionic, anionic or cationic surfactants. Examples of suitable anionic, non-ionic and cationic surfactants are listed in WO 97/34485 on pages 7 and 8.

Preferred surface-active substances are anionic surfactants of the dodecylbenzylsulfonate type, especially the calcium salts thereof, and also non-ionic surfactants of the fatty alcohol ethoxylate type. Special preference is given to ethoxylated $C_{12}$-$C_{22}$ fatty alcohols having a degree of ethoxylation of from 5 to 40. Examples of commercially available preferred surfactants are the Genapol types (Clariant AG, Muttenz, Switzerland).

The concentration of the surface-active substances based on the total additive is generally from 1 to 30% by weight.

Examples of oil additives consisting of mixtures of oils or mineral oils or derivatives thereof with surfactants are Edenor ME SU®, Emery 2231® (Henkel subsidiary company Cognis GmbH, Germany), Turbocharge® (Zeneca Agro, Stoney Creek, Ontario, Canada) or, more especially, Actipron® (BP Oil UK Limited, GB).

The addition of an organic solvent to the oil additive/ surfactant mixture can, furthermore, bring about a further increase in action. Suitable solvents are, for example Solvesso® (ESSO) or Aromatic Solvent® (Exxon Corporation) types.

The concentration of those solvents can be from 10 to 80%, by weight, of the total weight.

Such oil additives, which are also described, for example, in U.S. Pat. No. 4,834,908, are especially preferred for the composition according to the invention. An especially preferred oil additive is known under the name MERGE®, can be obtained from the BASF Corporation and is basically described, for example, in U.S. Pat. No. 4,834,908 in col. 5, as Example COC-1. A further oil additive that is preferred according to the invention is SCORE® (Novartis Crop Protection Canada).

In the composition according to the invention, the amounts of oil additive employed are generally from 0.01 to 2%, based on the spray mixture. The oil additive can, for example, be added to the spray tank in the desired concentration after the spray mixture has been prepared.

The invention relates also to a method for the selective control of weeds and grasses in crops of useful plants, which method comprises treating the useful plants, seeds or cuttings thereof or the area of cultivation thereof with a herbicidal composition that comprises a mixture of a) a herbicidally effective amount of formula I,
b) an amount, effective for herbicide synergy, of mesosulfuron, mesotrione or flufenacet,
c) an amount, effective for herbicide antagonism, of a safener selected from cloquintocet-mexyl and mefenpyr-diethyl; and, optionally, d) an additive comprising an oil of vegetable or animal origin, a mineral oil, alkyl esters of such oils, or mixtures of such oils and oil derivatives.

The compositions according to the invention are suitable for all methods of application that are customary in agriculture, for example pre-emergence application, post-emergence application and seed dressing.

In the case of seed dressing, from 0.001 to 10 g of safener/kg of seed, preferably from 0.05 to 6 g of safener/kg of seed, are generally applied. When the safener is applied in liquid form shortly before sowing, with swelling of the seed, it is advantageous to use safener solutions that comprise the active ingredient in a concentration of from 1 to 10 000 ppm, preferably from 10 to 1000 ppm.

For application, the safeners used according to the invention or combinations of those safeners with the herbicides and, optionally, the oil additives are processed, together with the adjuvants conventionally employed in formulation technology, into formulations, for example into emulsifiable concentrates, coatable pastes, directly sprayable or dilutable solutions, dilute emulsions, wettable powders, soluble powders, dusts, granules or microcapsules.

Such formulations are described, for example, in WO 97/34485, on pages 9 to 13. The formulations are prepared in known manner, for example by intimately mixing and/or grinding the active ingredients with liquid or solid formulation adjuvants, for example solvents or solid carriers. Furthermore, surface-active compounds (surfactants) may additionally be used in the preparation of the formulations. Solvents and solid carriers suitable for that purpose are mentioned, for example, in WO 97/34485 on page 6.

Depending on the nature of the compound of formula I being formulated, suitable surface-active compounds are non-ionic, cationic and/or anionic surfactants and mixtures of surfactants having good emulsifying, dispersing and wetting properties. Examples of suitable anionic, non-ionic and cationic surfactants are listed, for example, in WO 97/34485 on pages 7 and 8. Furthermore, the surfactants customarily employed in formulation technology, which are described, inter alia, in "Mc Cutcheon's Detergents and Emulsifiers Annual" MC Publishing Corp., Ridgewood N.J., 1981, Stache, H., "Tensid-Taschenbuch", Carl Hanser Verlag, Munich/Vienna, 1981, and M. and J. Ash; "Encyclopedia of Surfactants", Vol I-III, Chemical Publishing Co., New York, 1980-81, are also suitable for preparation of the herbicidal compositions according to the invention.

The herbicidal formulations generally comprise from 0.1 to 99% by weight, especially from 0.1 to 95% by weight, of active ingredient mixture comprising the compound of formula I, the second synergistically effective herbicide and, optionally, the safeners used in accordance with the invention, from 0 to 2% by weight of the oil additive used in accordance with the invention, from 1 to 99.9% by weight of a solid or liquid formulation adjuvant and from 0 to 25% by weight, especially from 0.1 to 25% by weight, of a surfactant. Whereas commercial products will preferably be formulated as concentrates, the end user will normally employ dilute formulations.

The compositions may also comprise further additives such as stabilisers, for example vegetable oils or epoxidised vegetable oils (epoxidised coconut oil, rapeseed oil or soybean oil), antifoams, for example silicone oil, preservatives, viscosity regulators, binders, tackifiers, and also fertilisers or other active ingredients. There are various suitable methods and techniques for using the safeners or compositions comprising them for protecting cultivated plants against harmful effects of the herbicides; the following are examples:

i) Seed Dressing a) Dressing the seeds with a wettable powder formulation of safener active ingredient by shaking in a vessel until the formulation is uniformly distributed over the seed surface (dry dressing). Approximately from 1 to 500 g of safener active ingredient according to the invention (from 4 g to 2 kg of wettable powder) are used per 100 kg of seed.

b) Dressing the seeds with an emulsifiable concentrate of safener according to method a) (wet dressing).

c) Dressing by immersing the seed in a liquid formulation comprising from 100 to 1000 ppm of safener for from 1 to 72 hours and, if desired, subsequently drying the seeds (immersion dressing).

Dressing the seed or treating the germinated seedlings are naturally the preferred methods of application because the treatment with the active ingredient is directed wholly at the target crop. Generally from 1 to 1000 g of antidote, preferably from 5 to 250 g of antidote, are used per 100 kg of seed, although, depending on the method employed, which also allows the addition of other active ingredients or micronutrients, amounts that exceed or fall short of the specified concentration limits may be employed (repeat dressing).

ii) Application in the Form of a Tank Mixture

A liquid formulation of a mixture of antidote and herbicide (ratio of the one to the other from 20:1 to 1:100) is used, the rate of application of herbicide being from 0.005 to 5.0 kg per hectare. The oil additive can be added to the tank mixture in an amount of, preferably, from 0.01 to 2% by weight. Such tank mixtures are applied before or after sowing.

iii) Application to the Seed Furrow

The safener is introduced into the open, sown seed furrow in the form of an emulsifiable concentrate, a wettable powder or granules. After the seed furrow has been covered, the herbicide, optionally in combination with the oil additive, is applied pre-emergence in the normal manner.

iv) Controlled Release of the Active Ingredient

The safener is applied in solution to granulated mineral carriers or polymerised granules (urea-formaldehyde) and dried. If desired, a coating may be applied (coated granules) which enables the active ingredient to be released in metered amounts over a predetermined period of time.

Preferred formulations have especially the following compositions (%=percent by weight; 'active ingredient mixture' denotes the mixture of compound of formula I with the synergistically effective second herbicide and, optionally, with the safeners and/or oil additives according to the invention.

Emulsifiable Concentrates:
active ingredient mixture: from 1 to 90%, preferably from 5 to 20%
surface-active agent: from 1 to 30%, preferably from 10 to 20%
liquid carrier: from 5 to 94%, preferably from 70 to 85%

Dusts:
active ingredient mixture: from 0.1 to 10%, preferably from 0.1 to 5%
solid carrier: from 99.9 to 90%, preferably from 99.9 to 99%

Suspension Concentrates:
active ingredient mixture: from 5 to 75%, preferably from 10 to 50%
water: from 94 to 24%, preferably from 88 to 30%
surface-active agent: from 1 to 40%, preferably from 2 to 30%

Wettable Powders:
active ingredient mixture: from 0.5 to 90%, preferably from 1 to 80%
surface-active agent: from 0.5 to 20%, preferably from 1 to 15%
solid carrier: from 5 to 95%, preferably from 15 to 90%

Granules:

active ingredient mixture: from 0.1 to 30%, preferably from 0.1 to 15% solid carrier: from 99.5 to 70%, preferably from 97 to 85%

The Examples that follow illustrate the invention further. They do not limit the invention.

Formulation Examples for Mixtures of Herbicides and, Optionally, Safener and Oil Additive (%=Percent by Weight)

| F1. Emulsifiable concentrates | a) | b) | c) | d) |
|---|---|---|---|---|
| active ingredient mixture | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |
| octylphenol polyglycol ether (7–8 mol of ethylene oxide) | — | 4% | — | 2% |
| cyclohexanone | — | — | 10% | 20% |
| aromatic $C_9$–$C_{12}$ hydrocarbon mixture | 85% | 78% | 55% | 16% |

Emulsions of any desired concentration can be prepared from such concentrates by dilution with water.

| F2. Solutions | a) | b) | c) | d) |
|---|---|---|---|---|
| active ingredient mixture | 5% | 10% | 50% | 90% |
| 1-methoxy-3-(3-methoxy-propoxy)-propane | — | 20% | 20% | — |
| polyethylene glycol (mol. wt. 400) | 20% | 10% | — | — |
| N-methyl-2-pyrrolidone | — | — | 30% | 10% |
| aromatic $C_9$–$C_{12}$ hydrocarbon mixture | 75% | 60% | — | — |

The solutions are suitable for application in the form of micro-drops.

| F3. Wettable powders | a) | b) | c) | d) |
|---|---|---|---|---|
| active ingredient mixture | 5% | 25% | 50% | 80% |
| sodium lignosulfonate | 4% | — | 3% | — |
| sodium lauryl sulfate | 2% | 3% | — | 4% |
| sodium diisobutylnaphthalenesulfonate | — | 6% | 5% | 6% |
| octylphenol polyglycol ether (7–8 mol of ethylene oxide) | — | 1% | 2% | — |
| highly dispersed silicic acid | 1% | 3% | 5% | 10% |
| kaolin | 88% | 62% | 35% | — |

The active ingredient is mixed thoroughly with the adjuvants and the mixture is thoroughly ground in a suitable mill, affording wettable powders which can be diluted with water to give suspensions of any desired concentration.

| F4. Coated granules | a) | b) | c) |
|---|---|---|---|
| active ingredient mixture | 0.1% | 5% | 15% |
| highly dispersed silicic acid | 0.9% | 2% | 2% |
| inorganic carrier material (diameter 0.1–1 mm) | 99.0% | 93% | 83% | for example $CaCO_3$ or $SiO_2$

The active ingredient is dissolved in methylene chloride, the solution is applied to the carrier by spraying, and the solvent is subsequently evaporated off in vacuo.

| F5. Coated granules | a) | b) | c) |
|---|---|---|---|
| active ingredient mixture | 0.1% | 5% | 15% |
| polyethylene glycol (mol. wt. 200) | 1.0% | 2% | 3% |
| highly dispersed silicic acid | 0.9% | 1% | 2% |
| inorganic carrier material (diameter 0.1–1 mm) | 98.0% | 92% | 80% | for example $CaCO_3$ or $SiO_2$

The finely ground active ingredient is uniformly applied, in a mixer, to the carrier material moistened with polyethylene glycol, yielding non-dusty coated granules.

| F6. Extruder granules | a) | b) | c) | d) |
|---|---|---|---|---|
| active ingredient mixture | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed with the adjuvants, and the mixture is ground, moistened with water, extruded and then dried in a stream of air.

| F7. Dusts | a) | b) | c) |
|---|---|---|---|
| active ingredient mixture | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

| F8. Suspension concentrates | a) | b) | c) | d) |
|---|---|---|---|---|
| active ingredient mixture | 3% | 10% | 25% | 50% |
| ethylene glycol | 5% | 5% | 5% | 5% |
| nonylphenol polyglycol ether (15 mol of ethylene oxide) | — | 1% | 2% | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground active ingredient is intimately mixed with the adjuvants, giving a suspension concentrate from which suspensions of any desired concentration can be obtained by dilution with water.

It is often more practical to formulate the herbicides (optionally in combination with the oil additive) and the safener separately and then, shortly before application, to bring them together in the applicator in the desired mixing ratio in the form of a "tank mixture" in water. The herbicides and the safener can also be formulated separately and, shortly before application, brought together in the applicator in the desired mixing ratio in the form of a "tank mixture" in water, with the oil additive being added thereafter.

The herbicidally selective action of the compositions according to the invention is illustrated in the following Examples.

BIOLOGICAL EXAMPLES

Example B1

Post-emergence Test

The test plants are grown in pots under greenhouse conditions until a post-application stage. A standard soil is used as cultivation substrate. At a post-emergence stage, the herbicides, both on their own and in admixture with safeners and/or oil additives, are applied to the test plants or to cultivated plants seed-dressed with safeners. The application is carried out using an emulsion (prepared from an emulsifiable concentrate (Example F1, c)) of the test substances. The rates of application depend on the optimum concentrations ascertained under field conditions or greenhouse conditions. The tests are evaluated after from 2 to 4 weeks (100% action=complete destruction, 0% action=no phytotoxic action).

What is claimed is:

1. A herbicidal composition that, in addition to comprising customary inert formulation adjuvants, comprises as active ingredient a mixture of
   a) a herbicidally effective amount of pinoxaden; and
   b) an amount, effective for herbicide synergy, of at least one herbicide selected from mesosulfuron, and flufenacet.

2. A composition according to claim 1, which further comprises c) an amount, effective for herbicide antagonism, of a safener selected from cloquintocet-mexyl and mefenpyr-diethyl.

3. A composition according to claim 1, which further comprises d) an additive comprising an oil of vegetable or animal origin, a mineral oil, alkyl esters of said oils or mixtures of said oils and alkyl esters of said oils.

4. A method for the selective control of weeds and grasses in crops of useful plants, which comprises treating the useful plants, seeds or cuttings thereof, or the area of cultivation thereof, with a composition according to claim 1.

5. A method according to claim 4, wherein the crops of useful plants are cereals.

* * * * *